United States Patent
Carrano et al.

(10) Patent No.: US 9,675,973 B2
(45) Date of Patent: *Jun. 13, 2017

(54) SPECIMEN DELIVERY APPARATUS

(71) Applicant: Paratus Diagnostics, LLC, Austin, TX (US)

(72) Inventors: John C. Carrano, Austin, TX (US); Roland Schneider, Austin, TX (US); John J. Carrano, Austin, TX (US)

(73) Assignee: PARATUS DIAGNOSTICS, LLC, Austin, TX (US)

( * ) Notice: Subject to any disclaimer, the term of this patent is extended or adjusted under 35 U.S.C. 154(b) by 372 days.

This patent is subject to a terminal disclaimer.

(21) Appl. No.: 13/918,877

(22) Filed: Jun. 14, 2013

(65) Prior Publication Data

US 2016/0001283 A1    Jan. 7, 2016

Related U.S. Application Data

(60) Provisional application No. 61/659,431, filed on Jun. 14, 2012.

(51) Int. Cl.
*B01L 3/00* (2006.01)
*G01N 1/38* (2006.01)

(52) U.S. Cl.
CPC ........... *B01L 3/502* (2013.01); *B01L 2200/06* (2013.01); *B01L 2200/10* (2013.01); *B01L 2200/16* (2013.01); *B01L 2300/041* (2013.01); *B01L 2300/046* (2013.01); *B01L 2300/0636* (2013.01); *B01L 2300/087* (2013.01); *B01L 2300/0867* (2013.01); *B01L 2300/123* (2013.01); *B01L 2400/0481* (2013.01); *B01L 2400/0683* (2013.01); *G01N 1/38* (2013.01)

(58) Field of Classification Search
CPC ...... B01L 3/502; B01L 3/565; B01L 2300/10; B01L 2300/41; B01L 2300/46; B01L 2300/861; B01L 2300/123; B01L 3/50273; B01L 3/502715; B01L 3/5055
USPC ................ 422/404, 408–410, 412–414, 417; 73/262, 274, 279, 729.1, 864.74
See application file for complete search history.

(56) References Cited

U.S. PATENT DOCUMENTS

| | | | |
|---|---|---|---|
| 9,085,745 B2 * | 7/2015 | Eckelberry | C11B 3/005 |
| 2010/0120083 A1 * | 5/2010 | Ritzen | B01L 3/502715 435/30 |

* cited by examiner

*Primary Examiner* — Brian R. Gordon
(74) *Attorney, Agent, or Firm* — McGuireWoods LLP

(57) ABSTRACT

A specimen delivery apparatus includes a housing having a backplane. The backplane includes at least one fluid communication port. The housing has an open state and a closed state. A midplane has a cavity for holding a sample. The midplane is sealed within the housing when the housing is in the closed state. A first actuator is disposed to move fluid within the housing when the housing is in a closed state and the first bulb is actuated. Various embodiments provide for caching of the fluid as well as staging to permit further preparation of the specimen prior to delivery. Various features roil the fluid to assist in extraction, mixing, and transport of the sample with the fluid. A destructible seal prevents fluid communication through the fluid communication port while the seal is intact. Communication of fluid through the fluid communication port is enabled only when the destructible seal is not intact.

14 Claims, 14 Drawing Sheets

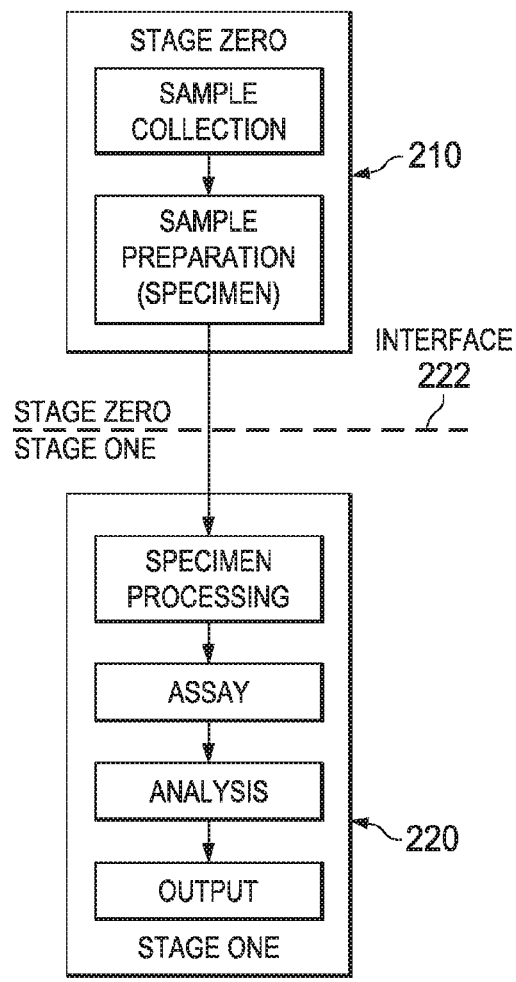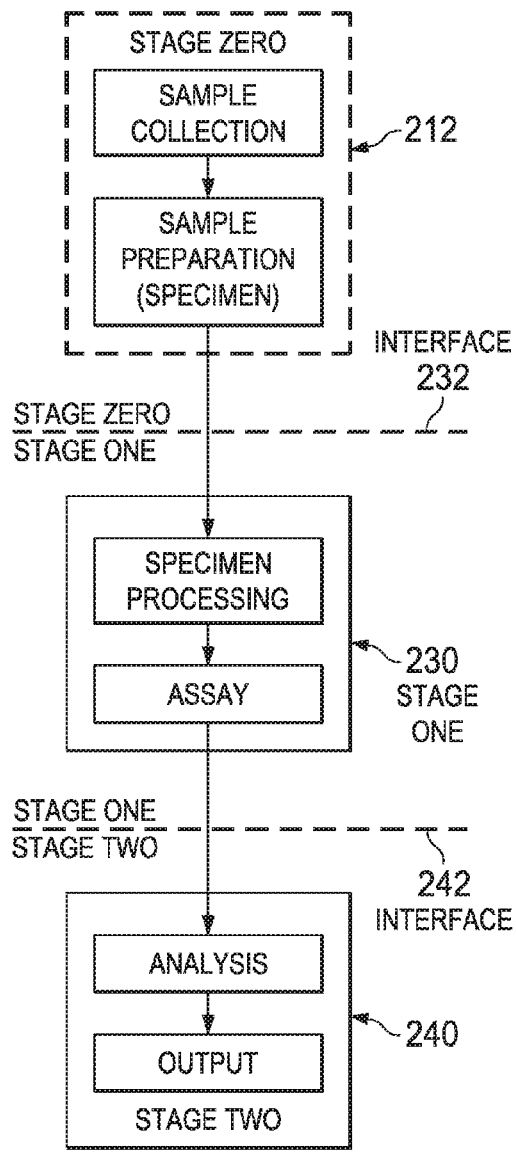
FIG. 2A
FIG. 2B

SPECIMEN DELIVERY APPARATUS

CROSS-REFERENCE TO RELATED APPLICATIONS

This application claims the benefit of provisional patent application No. 61/659,431, filed Jun. 14, 2012 which is incorporated herein by reference.

TECHNICAL FIELD

This invention relates to the field of medical diagnostics. In particular, this invention is drawn to a specimen delivery apparatus for in vitro medical diagnostic devices including point-of-care in vitro medical diagnostic devices.

SUMMARY

A specimen delivery apparatus includes a housing having a backplane. The backplane includes at least one fluid communication port. The housing has an open state and a closed state. A midplane has a cavity for holding a sample. The midplane is sealed within the housing when the housing is in the closed state. A first bulb is disposed to move fluid within the housing when the housing is in a closed state and the first bulb is actuated. A destructible seal prevents fluid communication through the fluid communication port while the seal is intact. Actuation of the first bulb communicates fluid through the fluid communication port when the destructible seal is not intact.

Another embodiment of a specimen delivery apparatus includes a housing having a backplane. The backplane includes at least one fluid communication port. The housing has an open state and a closed state. A midplane has a cavity for holding a sample. The midplane is sealed within the housing when the housing is in the closed state. The apparatus include a cache. A first actuator is disposed to move fluid within the apparatus when the housing is in a closed state and the first actuator is actuated. A portion of the fluid is cached by the cache upon actuation of the first actuator. A destructible seal prevents fluid communication through the fluid communication port while the seal is intact. Actuation of the first actuator communicates fluid other than the cached fluid through the fluid communication port when the destructible seal is not intact.

Another embodiment of a specimen delivery apparatus includes a housing having a backplane. The backplane includes at least one fluid communication port. The housing has an open state and a closed state. A midplane has a cavity for holding a sample. The midplane is sealed within the housing when the housing is in the closed state. A first bulb is disposed to move fluid within the apparatus when the housing is in a closed state and the first bulb is actuated. A latching apparatus co-operates with the housing to retain the first bulb in a compressed state when the first bulb is actuated. A destructible seal prevents fluid communication through the fluid communication port while the seal is intact. Actuation of the first bulb communicates fluid through the fluid communication port when the destructible seal is not intact.

Another embodiment of a specimen delivery apparatus includes a housing having a backplane. The backplane includes at least one fluid communication port. The housing has an open state and a closed state. A midplane has a cavity for holding a sample. The midplane is sealed within the housing when the housing is in the closed state. A fluid transport path includes features to roil fluid propelled through the fluid transport path. A first actuator is disposed to move fluid within the apparatus through at least a portion of the fluid transport path when the housing is in a closed state and the first actuator is actuated.

Another embodiment of a specimen delivery apparatus includes a housing having a backplane. The backplane includes at least one fluid communication port. The housing has an open state and a closed state. A midplane has a cavity for holding a sample. The midplane is sealed within the housing when the housing is in the closed state. The apparatus includes a staging chamber. A first actuator transports fluid within the apparatus to the staging chamber when the housing is in a closed state and the first actuator is actuated. A destructible seal preventing fluid communication through the fluid communication port while the seal is intact. Actuation of a second actuator transports fluid from the staging chamber through the fluid communication port when the destructible seal is not intact.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which:

FIGS. 2A and 2B illustrate embodiments of a modular staged point-of-care medical diagnostic system.

DETAILED DESCRIPTION

One approach to diagnosing medical ailments often entails steps such as collecting a sample from a patient, preparing a specimen from the sample, analyzing the specimen to assay the presence of various biological or chemical analytes, and interpreting the presence and amount of the analytes or their absence to derive a diagnosis. The study of samples of tissues and bodily fluids outside of the body is referred to as in vitro analysis.

Figure 1:
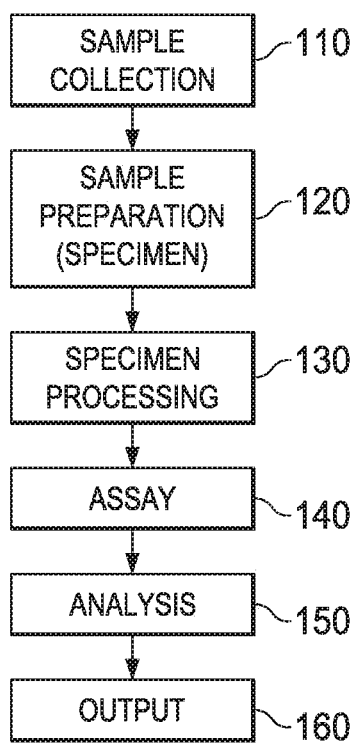
FIG. 1 illustrates one embodiment of a functional block diagram for performing a medical diagnosis.

FIG. 1 illustrates one embodiment of a process for performing an in vitro medical diagnosis. A sample of the tissue, fluid, or other bodily matter is collected in step 110. The sample is typically prepared in order to form a specimen in step 120. Preparation of the sample might include, for example, elution, mixing, or lysing in order to produce a specimen. In some cases, the sample serves as a specimen as collected. Further specimen processing may be performed at step 130.

After specimen processing, an assay is performed in step 140. In vitro analysis examines specimens for biological or chemical components. The assay may be qualitative, quantitative, or both. An analysis of the assay results is performed in step 150. The result of the analysis is then output in step 160.

The sample is collected from the patient at the point of care. The remaining steps may be performed on- or off-site or in any combination thereof. For example, samples or specimens may be sent to offsite laboratories with sophisticated equipment and highly trained laboratory personnel that process the specimen for analysis. To the extent these functions can be incorporated into a point-of-care medical diagnostic system, the cost and length of time required for diagnosing an ailment may be reduced considerably. The lead time for treatment as well as the cost for treatment may likewise be reduced. The medical diagnostic device may also indirectly protect populations other than the patient, particularly when dealing with detecting contagious diseases and assessing aggregate data for timely determining the onset or scope of an epidemic. Point-of-care medical diagnostic devices can offer significant healthcare benefits.

With respect to incorporating the process of FIG. 1 into a point-of-care medical diagnostic system, the functional blocks may be distributed across a number of components in order to enable economically efficient and practice efficient in vitro medical diagnostic devices.

Referring to FIGS. 2A and 2B, for example, in one embodiment of an in vitro medical diagnostic system, the functional blocks including sample acquisition and sample preparation are incorporated into stage zero component 210. Functional blocks including specimen processing, assay, analysis, and output are incorporated into one or more components.

In one embodiment, functional blocks including specimen processing and assay are incorporated into a stage one component 230. Functional blocks for analysis and output are incorporated into another component, stage two component 240. In an alternative embodiment, specimen processing, assay, analysis, and output are incorporated into a single component, the stage one component 220.

The distribution among various components enables staging of the medical diagnostic system to facilitate both practice and economic efficiency. Any component directly handling specimens will either have to be disposed of or alternatively sterilized before re-use.

In one embodiment, stages zero and one are disposable components. The analysis function is generally a computational function. If cost or practice efficient to do so, the analysis function may be incorporated into a disposable component. In one embodiment, however, the analysis function is incorporated into a subsequent stage ("stage two") that need not be disposed of. Modular staging enables the greatest flexibility to allocate diagnostic functions between components to realize practice and cost efficiencies.

The stages interface with a person or each other at various interfaces. In a point-of-care medical diagnostic system, physical coupling between stage one and any subsequent stage likely only needs to support electrical or optical signals. The electrical and signaling interface between stage one and any subsequent stage may be proprietary. Training requirements for coupling such stages together is minimal. Thus, for example, the stage one/stage two interface 242 might consist simply of an electrical connector.

The stage zero/stage one interface 222, 232 is likewise designed for ministerial level skills. Although different versions of specimen delivery systems (stage zero) might be necessary due to accommodate different types of samples or different specimen preparation processes, for example, the use of a standardized interface such as a snap-in or plug-in type of coupling ensures that only ministerial skill levels are needed to couple the specimen delivery system to the next modular stage of the point-of-care medical diagnostic system.

In contrast, the interface between the patient and stage one may be indirect and involve a number of steps that previously required significant skills or training and equipment. Acquisition of typical samples from a patient is largely a mechanical task and does not require significant training. Typical samples, for example, consist of fluids or tissue. Collection of these samples is performed by a clinician or provided by the patient using standard clinical techniques (e.g., blood, dried blood, urine, sputum, mucous, etc.).

Sample preparation can impose much greater training requirements. Sample preparation might be performed by a laboratorian and is susceptible to variations in user experience, skill set, and preparation environmental conditions. In addition, sample preparation often required additional equipment for measuring and mixing along with a separate inventory of the items that the sample would be mixed with.

A specimen delivery apparatus is proposed to reduce or eliminate the need for skilled practitioners or laboratory personnel. Standard clinical practices for obtaining samples from the patient may be utilized to collect the sample. Although the functions performed by the specimen delivery apparatus might qualify as complex, the function is largely abstracted from the user. In particular, the user performs low-complexity tasks (e.g., select an appropriate specimen delivery apparatus, place the sample in the specimen delivery apparatus, close the selected specimen delivery apparatus, attach the specimen delivery apparatus to a subsequent stage, and actuate a bulb on the specimen delivery apparatus). The specimen delivery apparatus may be configured to support various samples and sample preparation needs.

Figure 3A:
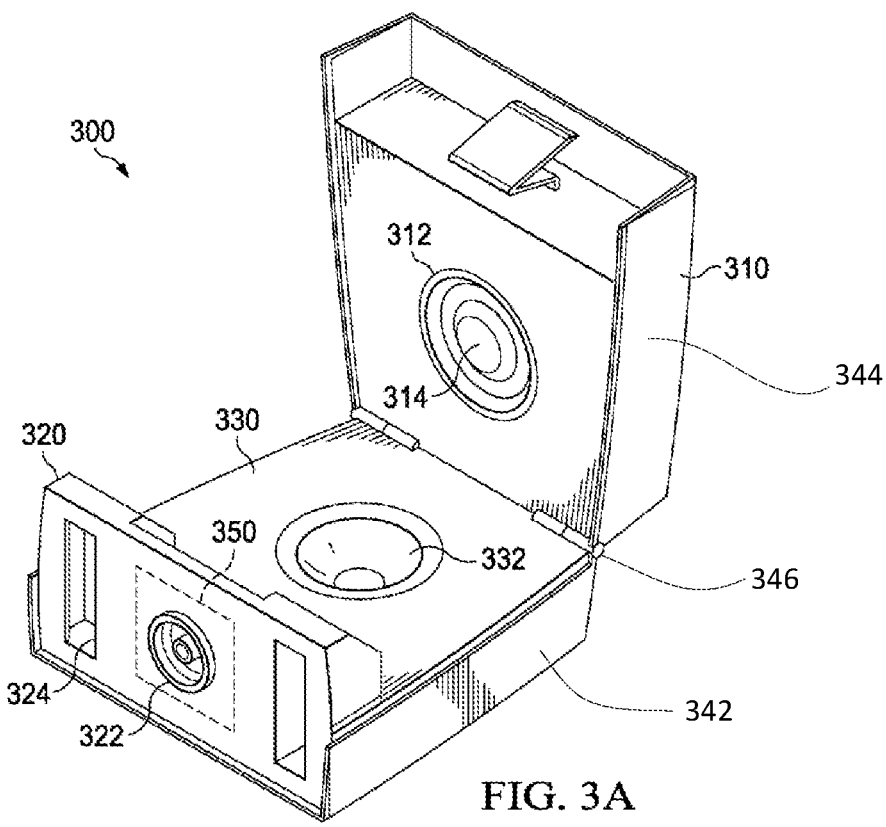
FIGS. 3A-3C illustrate embodiments of a specimen delivery apparatus.
Figure 3B:
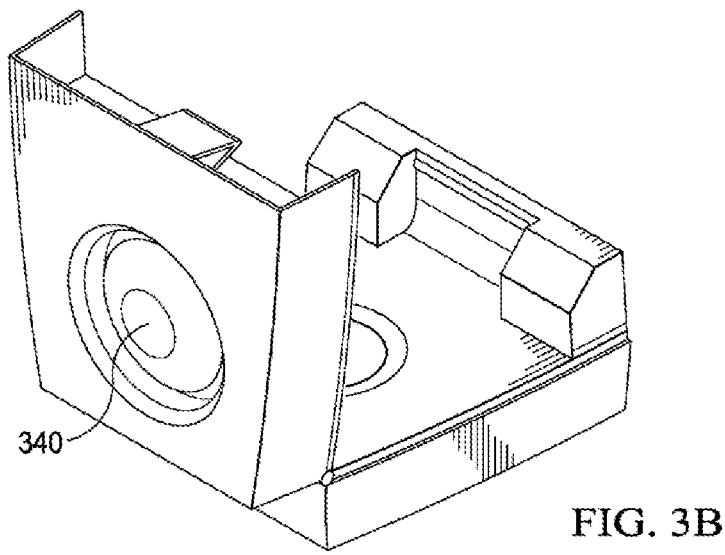
Figure 3C:
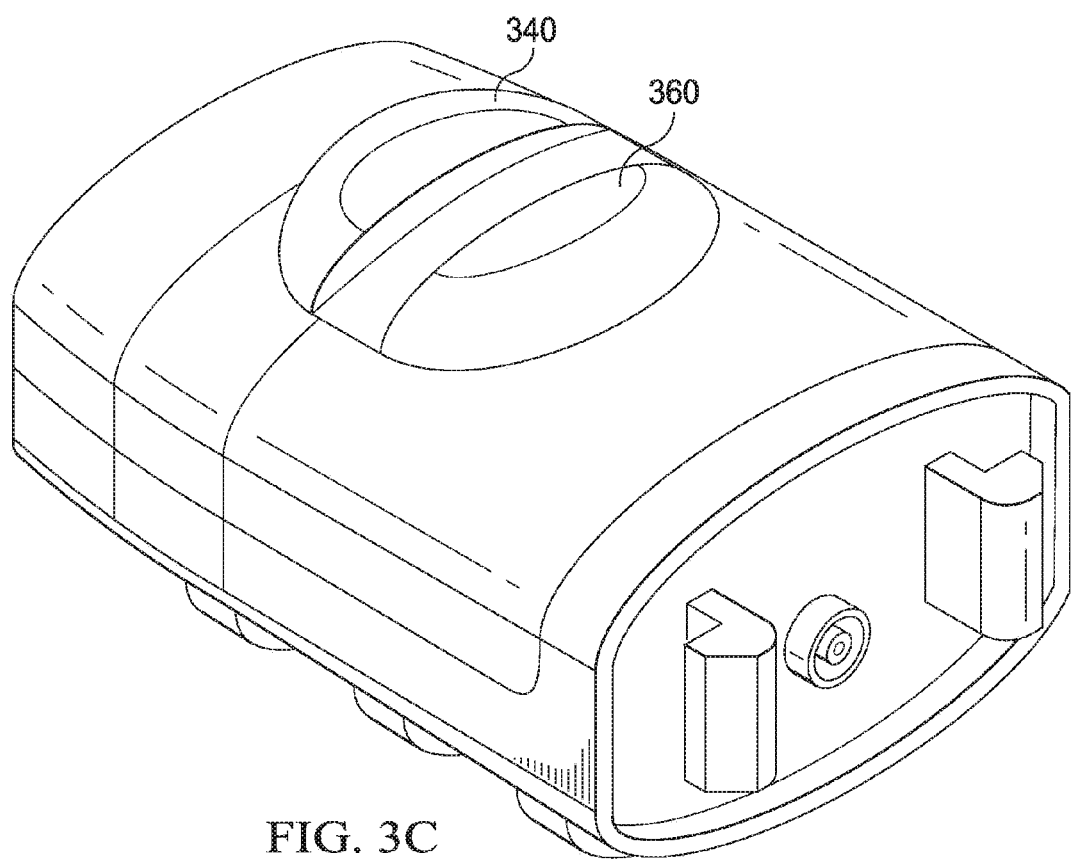

FIGS. 3A-3C illustrate an embodiment of a specimen delivery apparatus 300. The specimen delivery apparatus includes a housing 310 having a first portion 342 and a second portion 344 coupled at a hinge 346. The housing has an open state and a closed state. In one embodiment, the housing is hinged such that the housing may be closed by moving the second portion 344 toward the first portion 342. The housing includes a backplane 320, which includes at least one fluid communication port 322, and may thereby be referenced as in interfacing surface. A midplane 330 serves as an intermediate portion having a cavity 332 for holding a sample. The midplane 330 is sealed within and positioned between the first portion 342 and second portion 344 of the housing when the housing 310 is in the closed state.

In one embodiment, the housing includes locking features to secure the housing in a closed state once closed. Thus a sample may be placed in the housing in the open state. Once closed, the features prevent the housing from being opened back up. Such features aid in the containment of medical waste.

A first actuator 340 is disposed to move fluid within the housing when the housing is in the closed state and the first actuator is actuated. In the illustrated embodiment, the first actuator is a bulb and is referred to as first bulb 340. A destructible seal 350 prevents fluid communication through the fluid communication port while the seal is intact. Actuation of the first bulb communicates fluid through the fluid communication port when the destructible seal is not intact.

In one embodiment, the specimen delivery system includes a second actuator or second bulb 360. Alternate actuation of the first and second bulbs moves fluid within the housing when the destructible seal is intact. Actuation of the first or second bulb moves fluid through the fluid communication port when the destructible seal is not intact.

In one embodiment, a "locking" mechanism is employed for one or more bulbs. The locking mechanism maintains the bulb in a depressed position once actuated. One embodiment of the locking mechanism includes a shell covering a flexible portion of the bulb. The shell includes features to latch onto mating features of the housing when depressed. The locking mechanism prevents the specimen delivery apparatus from drawing or siphoning fluid back through the fluid communication port. The locking mechanism also serves to provide visual feedback indicative of a used specimen delivery apparatus. Another advantage of a bulb locking mechanism includes tactile feedback for the user: when the locking mechanism "snaps" into place and retains the bulb, the user may be confident that the user has completed the delivery task.

In one embodiment, the backplane includes at least one attachment point 324 for mechanically coupling the specimen delivery apparatus to a subsequent stage of the point-of-care medical diagnostic system. When coupled via the attachment point, the fluid communication port of the specimen delivery apparatus is aligned with a fluid communication port of the subsequent stage to enable fluid communication between the specimen delivery apparatus and the subsequent stage. In one embodiment, the attachment point includes features to prevent de-coupling of the specimen delivery apparatus and subsequent stage once coupled.

To facilitate sample preparation, the housing includes a blister pack retainer 312. A blister pack 314 containing a sample preparation fluid is placed in the blister pack retainer. In one embodiment, closing the housing causes the blister pack to burst and release its contents. In an alternative embodiment, the first bulb is disposed such that actuation of the first bulb when the housing is closed causes the blister pack to burst and release its contents.

The use of a blister pack substantially eliminates the need to have external laboratory equipment, supplies, or skilled personnel for sample preparation. The blister pack may be selected for the appropriate sample preparation.

In one embodiment, the blister pack contains a fluid for mixing with and carrying the sample in suspended, diluted, or dissolved form. In another embodiment, the blister pack contains a reagent such as a lysing agent to react with the sample. In one embodiment, the blister pack contains an elution buffer. In another embodiment, the blister pack contains an anti-coagulant. In yet another embodiment, the blister pack contains a solvent to enable extraction of the sample from any carrier it has adhered to. For example, a solvent may be appropriate to extract mucous or similar such samples from a swab.

In one embodiment, a fluid transport tube is coupled to carry fluid from the cavity to the fluid communication port. In one embodiment, the fluid transport tube is rifled to enhance mixing of fluids transported from the cavity to the fluid communication port.

Figure 4B:
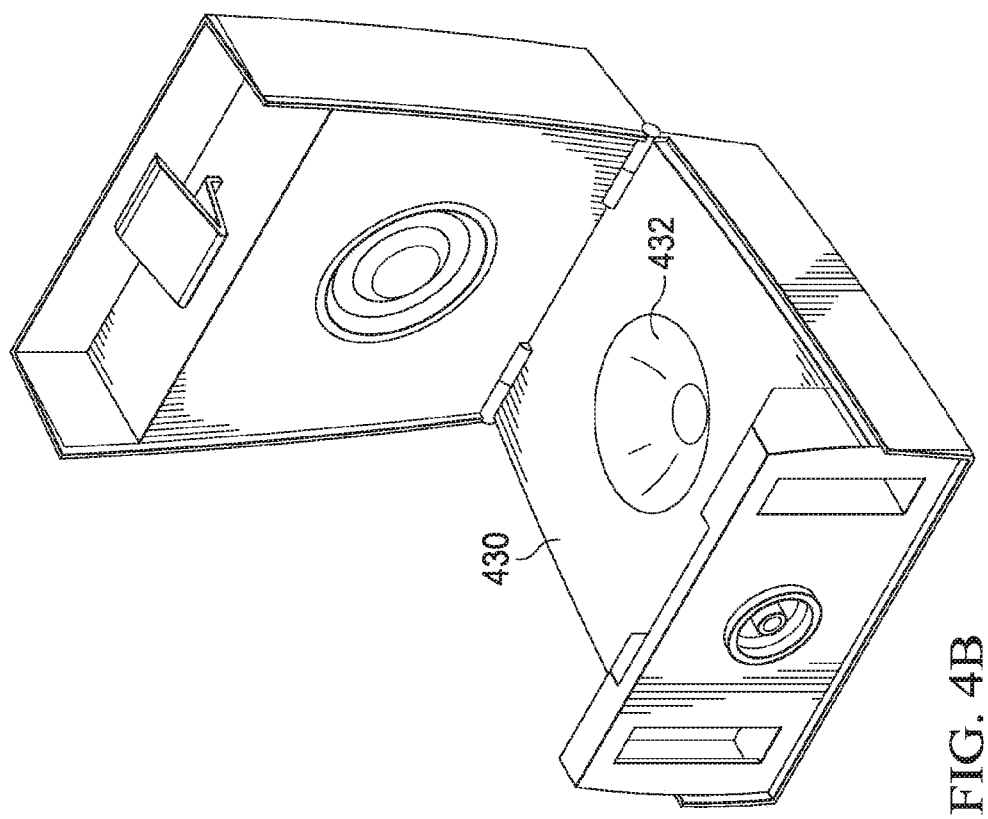
FIGS. 4A-4C illustrate variations on the form factor of the cavity of the specimen delivery apparatus midplane.
Figure 4A:
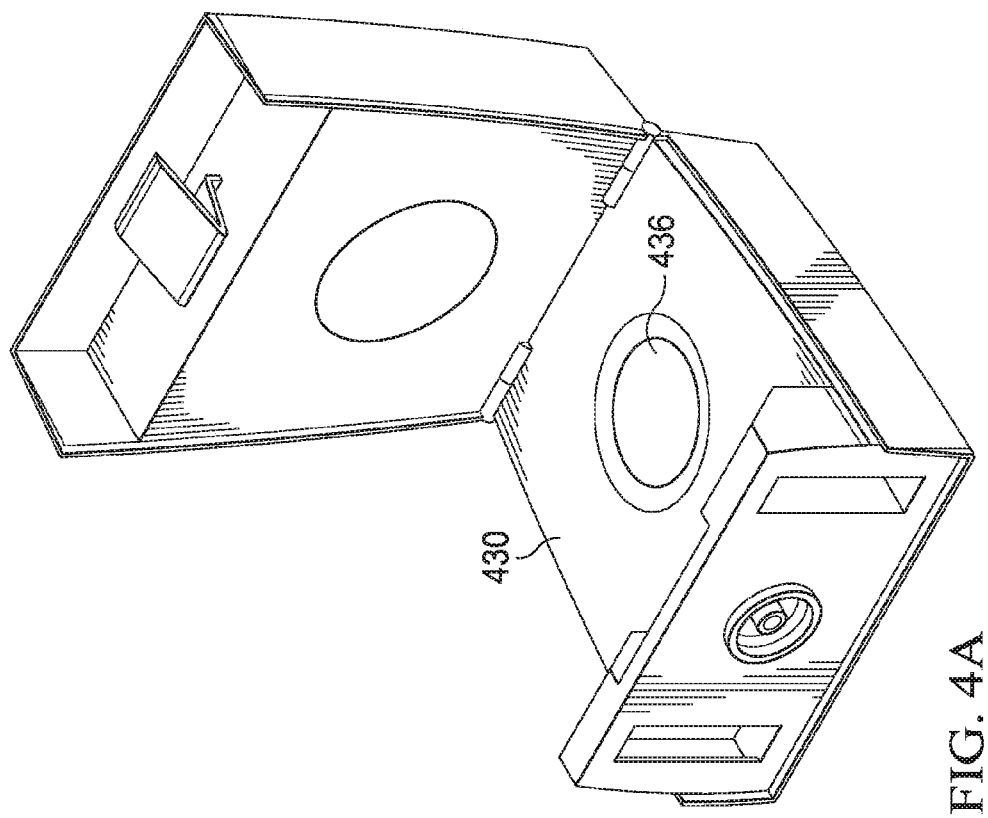
Figure 4C:
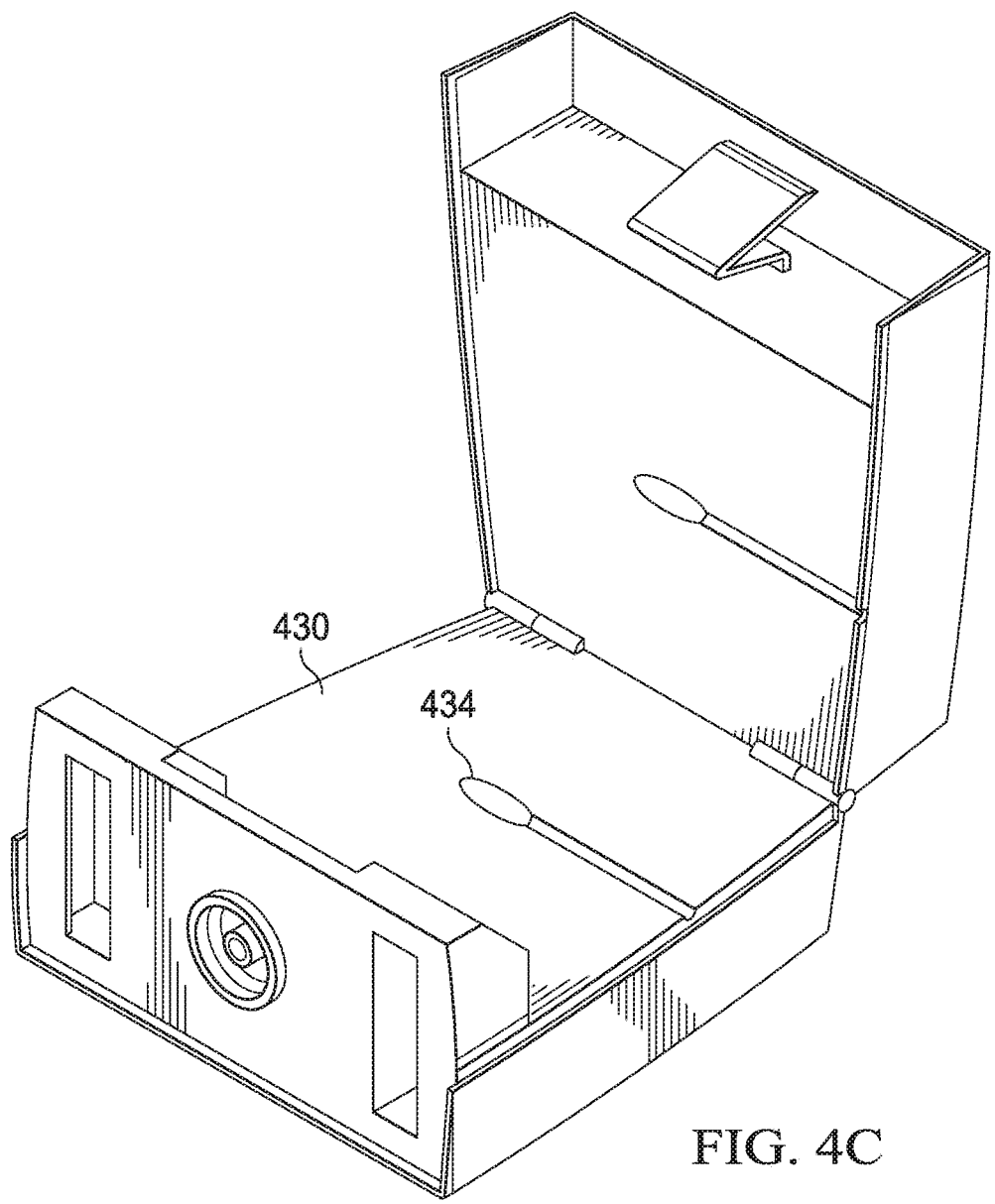

FIGS. 4A-4C illustrate variations on the form factor of the cavity of the midplane 430. The form factor is chosen to facilitate a particular clinical technique or volume associated with the sample being collected. Frequent sample types or sources include blood, urine, tissue, sputum, and mucous.

For example, a hemispheroidal cavity 432 may be appropriate for liquids such as urine or blood. A cavity having a longitudinal cross-sectional profile substantially the same as that of a swab 434 is used for samples collected by and carried by swab. In one embodiment, the midplane has an open cylindrically-shaped cavity 436.

Figure 5:
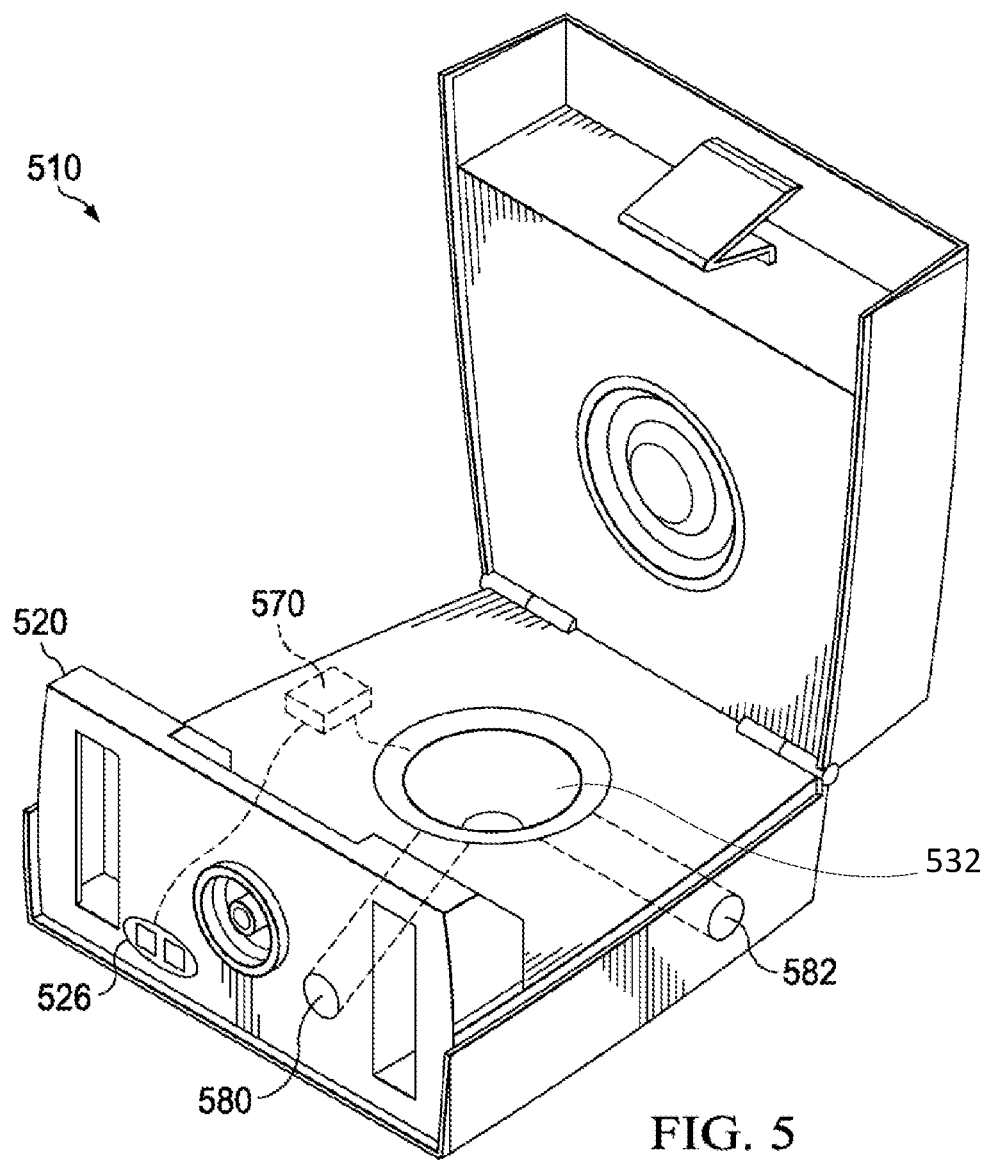
FIG. 5 illustrates another embodiment of the specimen delivery apparatus.

FIG. 5 illustrates another embodiment of the specimen delivery apparatus 510. Backplane 520 includes an electrical port 526 for communication of electrical power to an element 570 within the apparatus. In one embodiment, element 570 is a transducer coupled to the electrical port for applying at least one of a thermal, mechanical, acoustical, or optical energy to the fluid upon application of electrical power to the electrical port.

In one embodiment, the electrical port enables communication of electrical power directly to fluid within the cavity 532 of the apparatus upon application of electrical power to the electrical port. Such a feature may be used to enable lysis via pulsed application of power.

In one embodiment, element 570 is a heater for heating fluid within the apparatus upon application of power to the electrical port. Thermal energy may be used for lysis or sanitization. In one embodiment, element 570 is an acoustic transducer for application of acoustic energy to fluid within the apparatus. Acoustic energy may be used to create cavitation and heat within the fluid sufficient to cause lysis within various biological substances. In one embodiment, the acoustic transducer is a piezoelectric element.

The apparatus may include one or more optical ports 580, 582. In one embodiment, an optical port is included to enable inspection of the contents of the specimen delivery apparatus. In one embodiment, an optical port is included to enable the application of optical energy to the contents of the specimen delivery apparatus.

Figure 6:
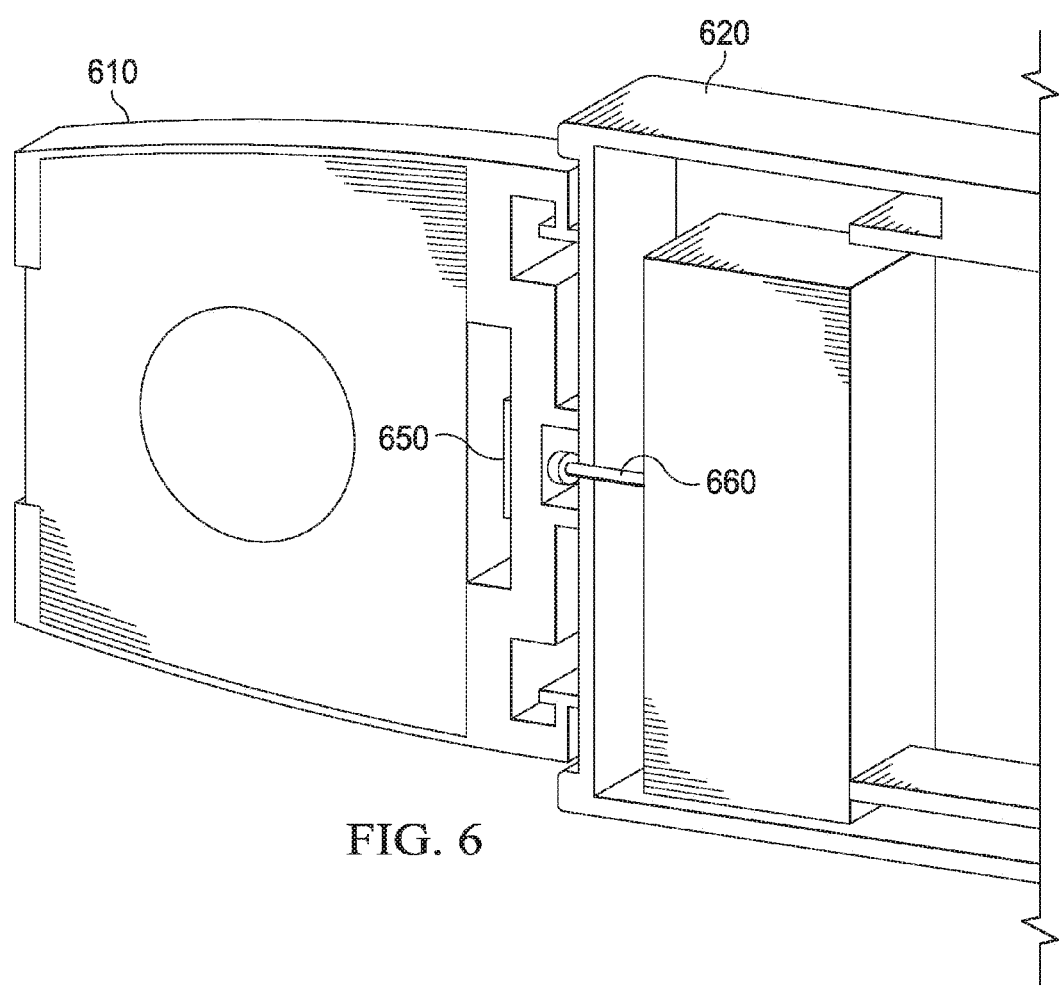
FIG. 6 illustrates attachment of the specimen delivery apparatus to another device.

FIG. 6 illustrates the attachment of the specimen delivery apparatus 610 to the next stage 620 of the point-of-care medical diagnostic system. Upon attachment, the destructible seal 650 is pierced (e.g., by piercing probe 660) such that it is no longer intact. Actuation of a bulb of the specimen delivery apparatus forces fluid communication of the specimen from the specimen delivery apparatus to the next stage of the point-of-care medical diagnostic system.

Figure 7A:
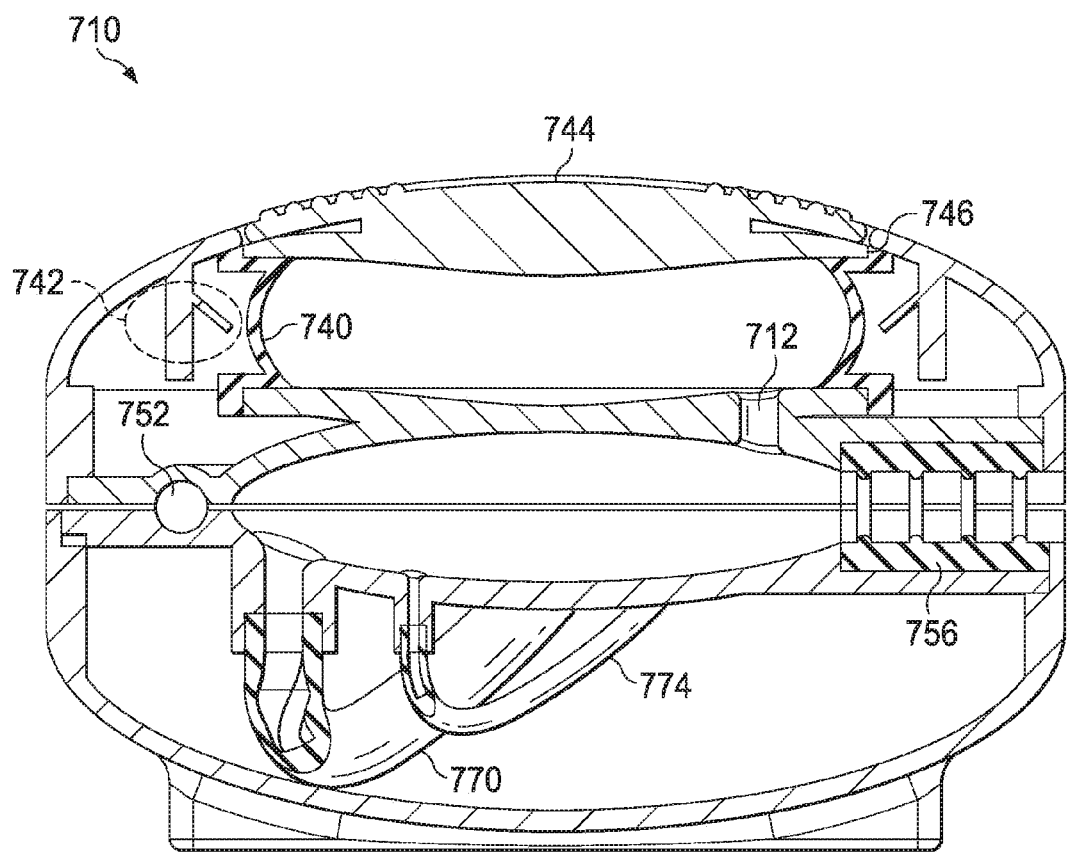
FIGS. 7A-7B illustrate a cross-section of one embodiment of a specimen delivery apparatus with a bulb locking mechanism
Figure 7B:
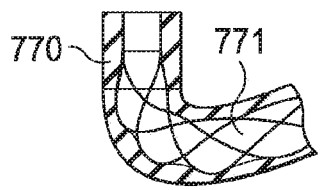

FIGS. 7A-7B illustrate a cross-section of one embodiment of the specimen delivery apparatus 710 with a bulb locking mechanism. The housing includes retaining apparatus 742 to maintain the bulb 740 in a depressed position once actuated. A shell 744 covers the flexible portion of the bulb.

The shell includes latching features 746 to latch onto or to be retained by the retaining apparatus. The locking mechanism prevents the specimen delivery apparatus from drawing or siphoning fluid back through the fluid communication port. Once the shell is depressed sufficiently to capture or to be captured by the retaining apparatus, the bulb will be maintained in a depressed position. The bulb locking mechanism provides tactile feedback for the user: when the locking mechanism "snaps" into place and retains the bulb, the user may be confident that the user has completed the delivery task. In addition, the locking mechanism provides visual feedback indicative of a used specimen delivery apparatus.

FIG. 7A also illustrates a midplane configured for a swab. One or more seals 752 serve to prevent the sample from escaping the sampling apparatus through unintended routes. In one embodiment, the midplane and housing include features that co-operate to form at least one swab shaft seal 756. The swab shaft seal(s) assist in preventing the sample from escaping along the shaft of the swab.

In one embodiment, rather than using a separate blister pack the bulb 740 may be filled with the fluid to be mixed with the sample. In the illustrated embodiment, the fluid is propelled through tube 712 into the sample chamber that is adapted for a swab.

The fluid transport path transports the fluid to a location internal or external to the specimen delivery apparatus. The fluid transport path may include a portion of the midplane as well as channels, tubes, or intermediate storage mechanisms. The fluid transport path itself may include features to facilitate extracting the sample and mixing the sample with the fluid to prepare and transport the specimen.

For example, the fluid transport path may include channels or fluid transport tube(s) 770, 774 to transport the fluid to a location internal or external to the specimen delivery apparatus. The channel or fluid transport tube(s) may be rifled or have rifling 771 as indicated by the callout for fluid transport tube 770 in order to enhance mixing and transport of the fluid and sample. Features such as the rifling cause the fluid and material carried by the fluid to roil. The roiling effect aids in mixing and transport.

In one embodiment, the specimen delivery apparatus includes a validation cache. The purpose of the cache is to retain a clinically relevant amount of the sample within the housing in order to permit independent testing. Fluid transport tube 770 carries the fluid to a fluid communication port. Fluid transport tube 774 carries fluid to the cache.

Figure 8A:
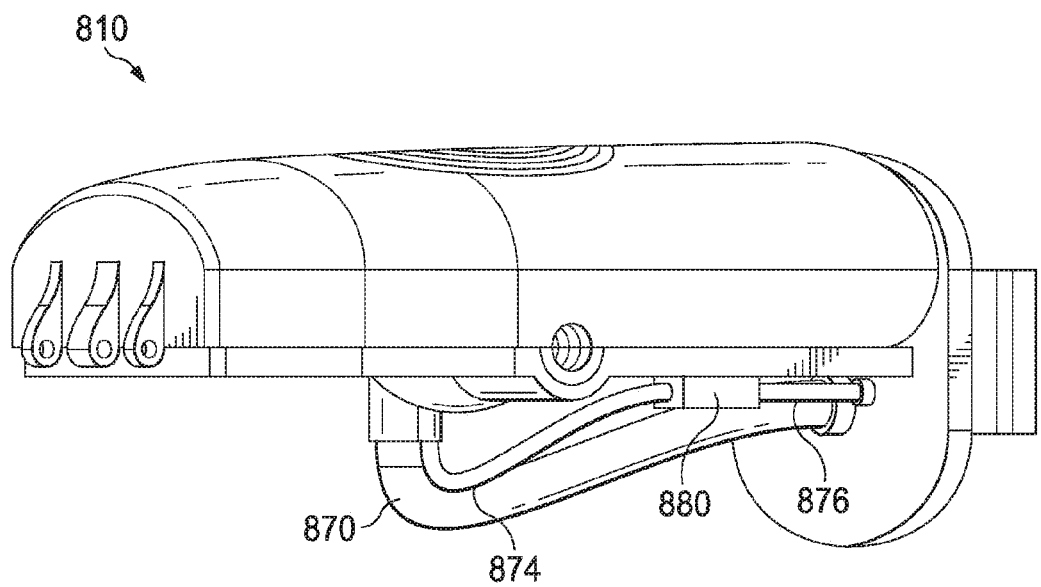
FIGS. 8A-8B illustrate an embodiment of the specimen delivery apparatus with a validation cache.
Figure 8B:
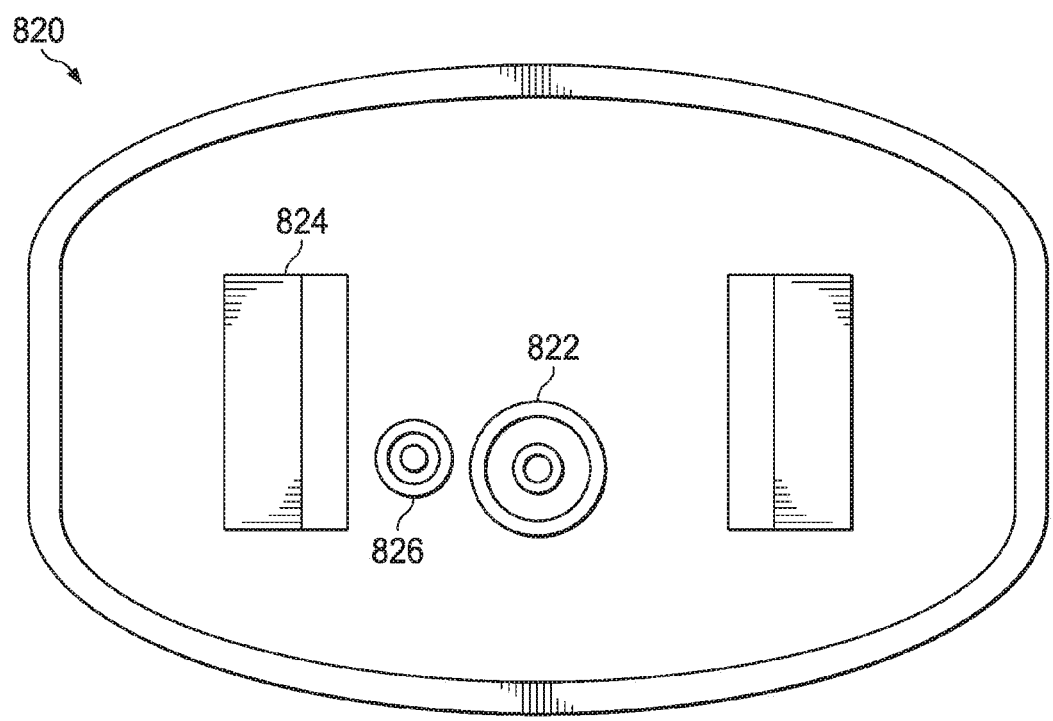

FIG. 8A illustrates a side view of a cutaway of one embodiment of the specimen delivery apparatus 810 including a validation cache 880, and FIG. 8B illustrates a front view of the backplane 820. FIG. 8A shows that a fluid transport tube 874 is provided to carry fluid to the cache. In one embodiment another fluid transport tube 876 carries fluid away from the cache. In alternative embodiments, the contents of the cache may be accessed by extraction through other apparatus such as a stopper as found with vials and ampules.

As shown in FIG. 8B, a front view of the backplane 820 illustrates the primary fluid communication port 822 to be used with next stage point of care. Generally although a fluid transport tube 876 might couple the cache to a cache fluid communication port 826, the next stage device utilizing the primary fluid communication port 822 will not be the same device that utilizes the cache fluid communication port 826. In the field, the attachment points 824 coupling the specimen delivery apparatus to the next stage prevent field separation of the specimen delivery apparatus and the next stage. In one embodiment, a special tool may be utilized to permit separation of the specimen delivery apparatus and the next stage in order for the validation lab to gain access to a cache fluid communication port 826 positioned on the backplane 820.

Figure 9:
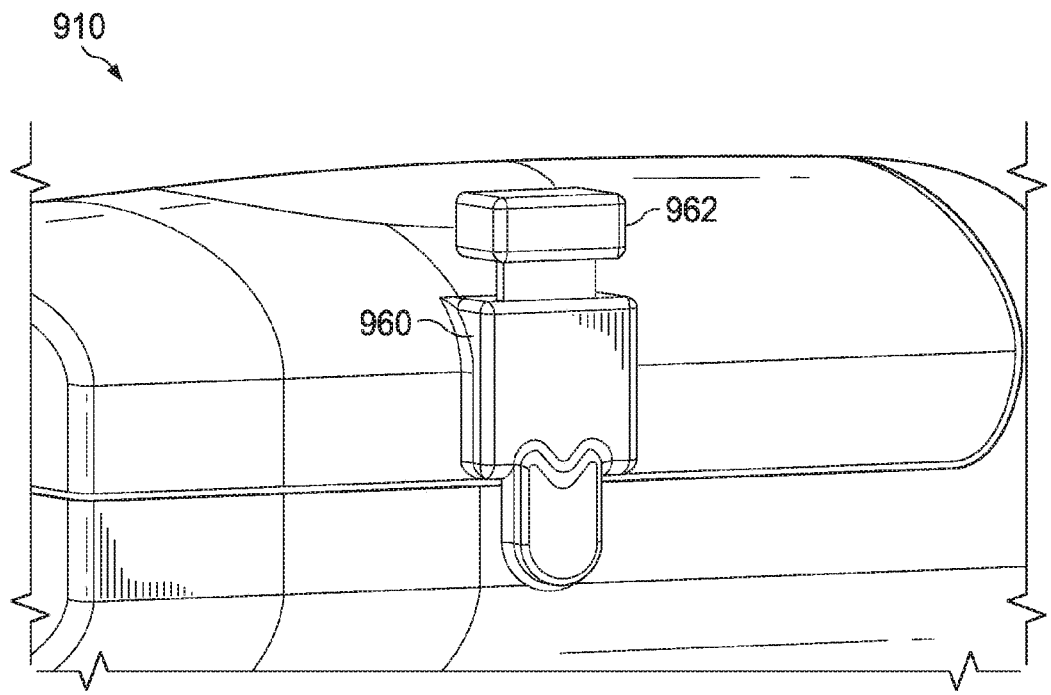
FIG. 9 illustrates one embodiment of a swab cutter for a specimen delivery apparatus.

The shaft portion of a swab is a nuisance once the sample is acquired and placed within the specimen delivery apparatus. A swab may have a pre-scored shaft to facilitate breaking off the shaft after the sample is disposed within the specimen delivery apparatus. Alternatively the specimen delivery apparatus may include a swab cutter to neatly trim away excess swab shaft material. FIG. 9 illustrates one embodiment of a swab cutter 960 for a specimen delivery apparatus 910. The swab cutter includes a blade (not shown) or other cutting apparatus coupled to the button 962. After placement of the swab in the specimen delivery apparatus and closing specimen delivery apparatus, the button 962 of the swab cutter may be depressed to sever the swab shaft.

The fluid transport path may be configured to accomplish goals in addition to transport. As addressed above, channels or fluid transport tubes can include rifling or other features to facilitate transport and mixing. In some cases, the sample may be carried by a tool such as a swab from which the sample must be stripped in order to prepare the specimen. When the specimen delivery apparatus is in the closed position, the swab is held within a chamber formed by the housing and the midplane cavity. In order to extract more sample from the swab, the chamber may include features to create a roiling effect when fluid is driven into the chamber. The chamber forms a portion of the fluid transport path. Thus the fluid transport path may include features to strip or extract, mix, and carry the sample when preparing the specimen.

Figure 10:
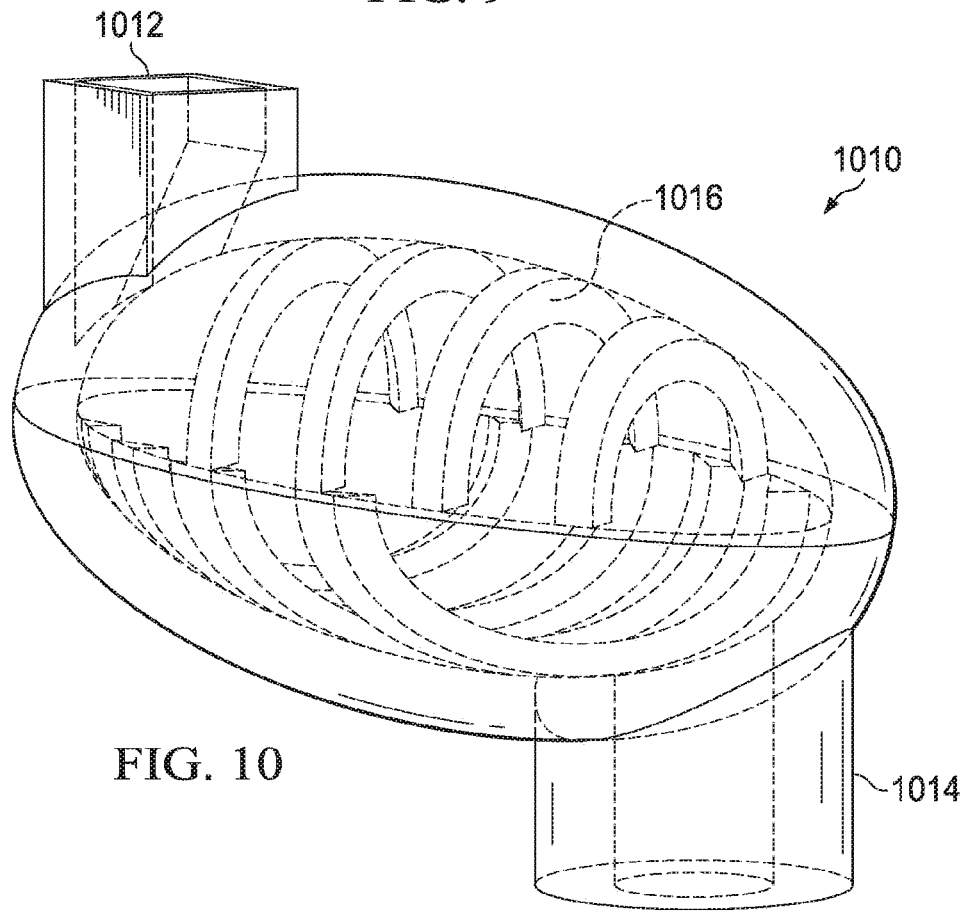
FIG. 10 illustrates one embodiment of a chamber containing a swab when the specimen delivery apparatus housing is in the closed position.

FIG. 10 illustrates the chamber 1010 containing the swab when the specimen delivery apparatus housing is in the closed position. The chamber includes an inlet port 1012 that receives fluid from the bulb or blister pack. The chamber includes an exit port 1014 for the fluid and sample to be carried to the remainder of the fluid transport path. The chamber has grooves, raised thresholds, or other features to direct the fluid. In the illustrated embodiment the features 1016 appear to form a helical or spiral structure.

Figure 11:
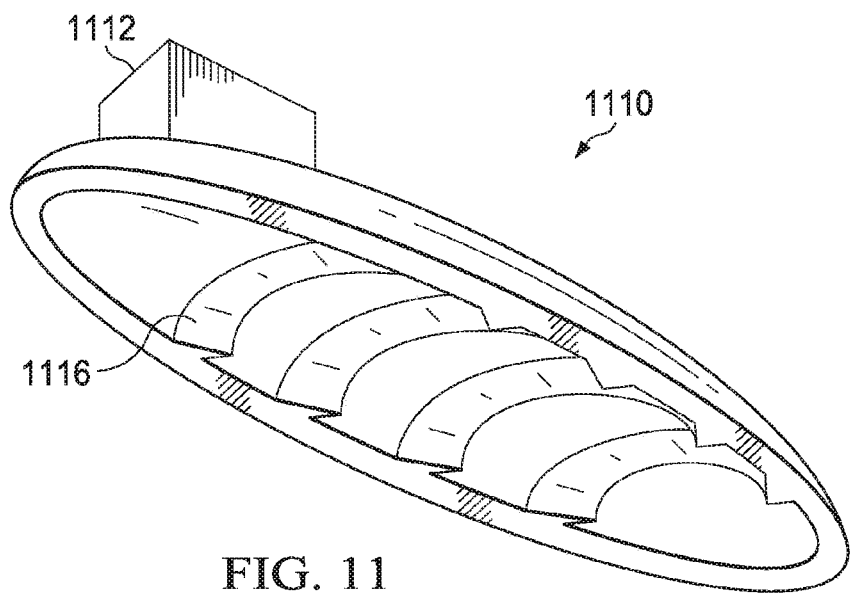
FIG. 11 illustrates one embodiment of the upper portion of the chamber of FIG. 10 with roiling features.
Figure 12:
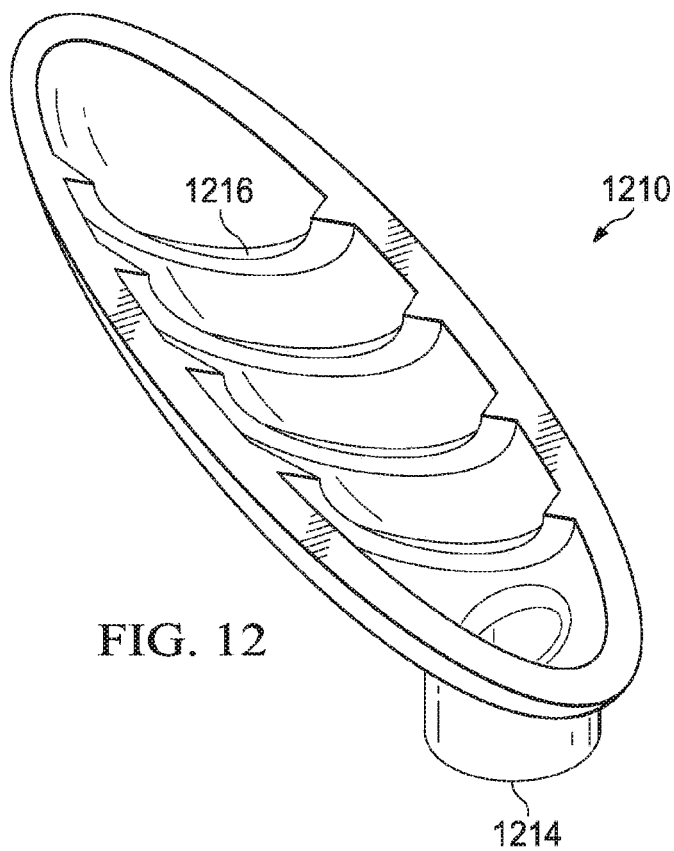
FIG. 12 illustrates one embodiment of the lower portion of the chamber of FIG. 10 with roiling features.

FIG. 11 illustrates one embodiment of the upper portion 1110 of the chamber including the inlet port 1112 and the grooved or raised features 1116 that form a portion of the fluid transport path. FIG. 12 illustrates one embodiment of the lower portion 1210 of the chamber including the exit port 1214 and the grooved or raised features 1216 that form a portion of the fluid transport path. The grooved or raised features of the chamber increase the shear forces of the fluid and direct the fluid across the surface of the swab to extract the sample from the swab. The roiling effect caused by these features also enhances mixing of the fluid with the sample.

Figure 13:
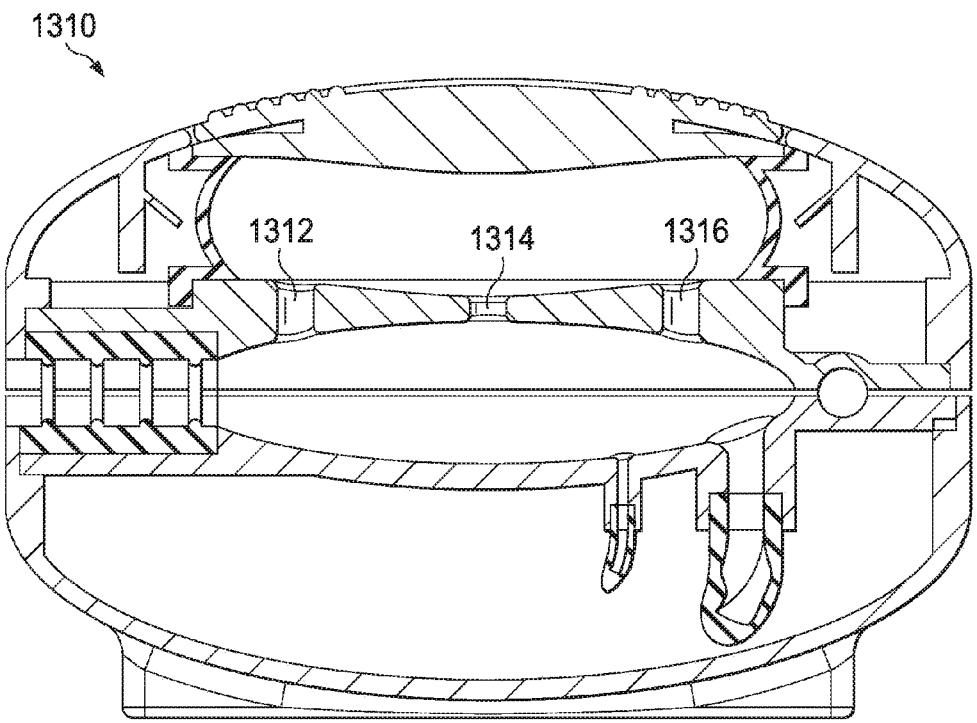
FIG. 13 illustrates one embodiment of a specimen delivery apparatus having multiple entry points for communicating fluid into the chamber.

The housing and midplane may be configured to provide for multiple entry points of fluid into the fluid transport path. FIG. 13 illustrates one embodiment of a specimen delivery apparatus 1310 having multiple entry points 1312, 1314, 1316 for communicating fluid from the bulb or blister pack into the sample chamber.

In one embodiment, the specimen delivery apparatus includes a staging chamber to separate the function of specimen preparation and specimen delivery to the next stage. For example, reagents in the transport fluid may require time beyond the transport time to fully act upon the sample. Electrical, thermal, or acoustic lysis may require time beyond the fluid transport time to complete.

Figure 14:
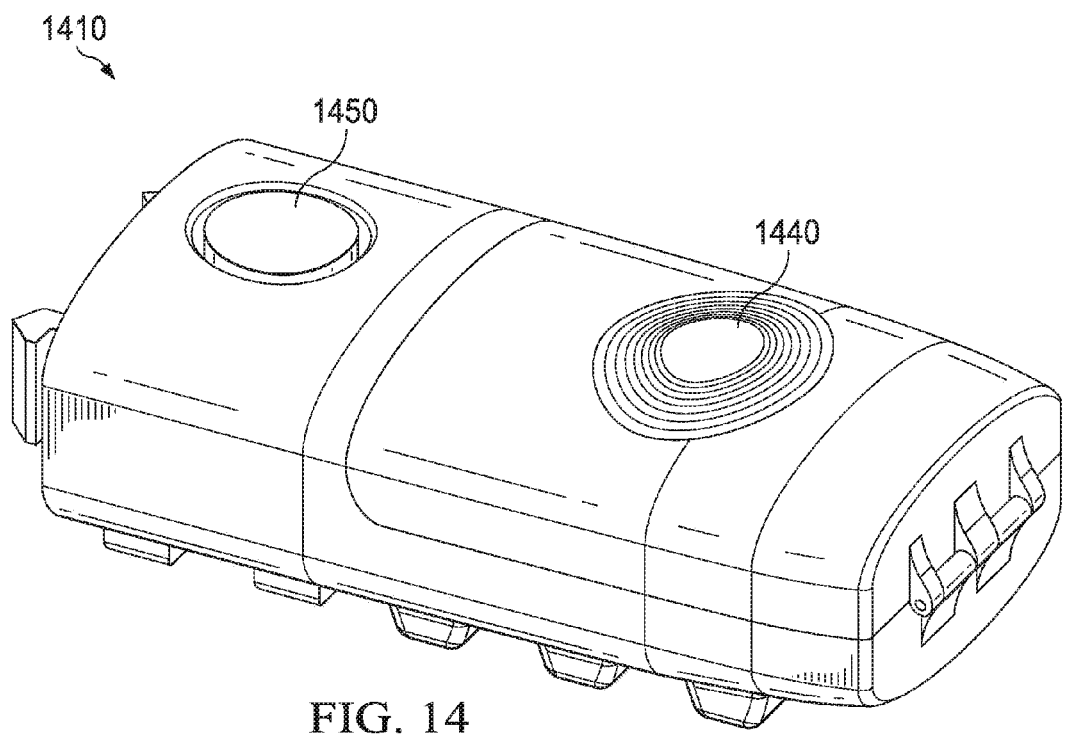
FIG. 14 illustrates one embodiment of a staging or "dual action" specimen delivery apparatus.

FIG. 14 illustrates one embodiment of a staging or "dual action" specimen delivery apparatus 1410. Depressing the first actuator 1440 performs some mixing of the sample with a fluid and transports the fluid with sample to a staging chamber (not shown). A second actuator 1450 propels the prepared specimen to the next stage. The first actuator may be a "bulb" as previously described in one embodiment. The second actuator may be a bulb or any other apparatus for driving the specimen from the chamber to the next stage through the fluid communication port of the specimen delivery apparatus. The first and second actuators are fluid transport actuators.

Figure 15:
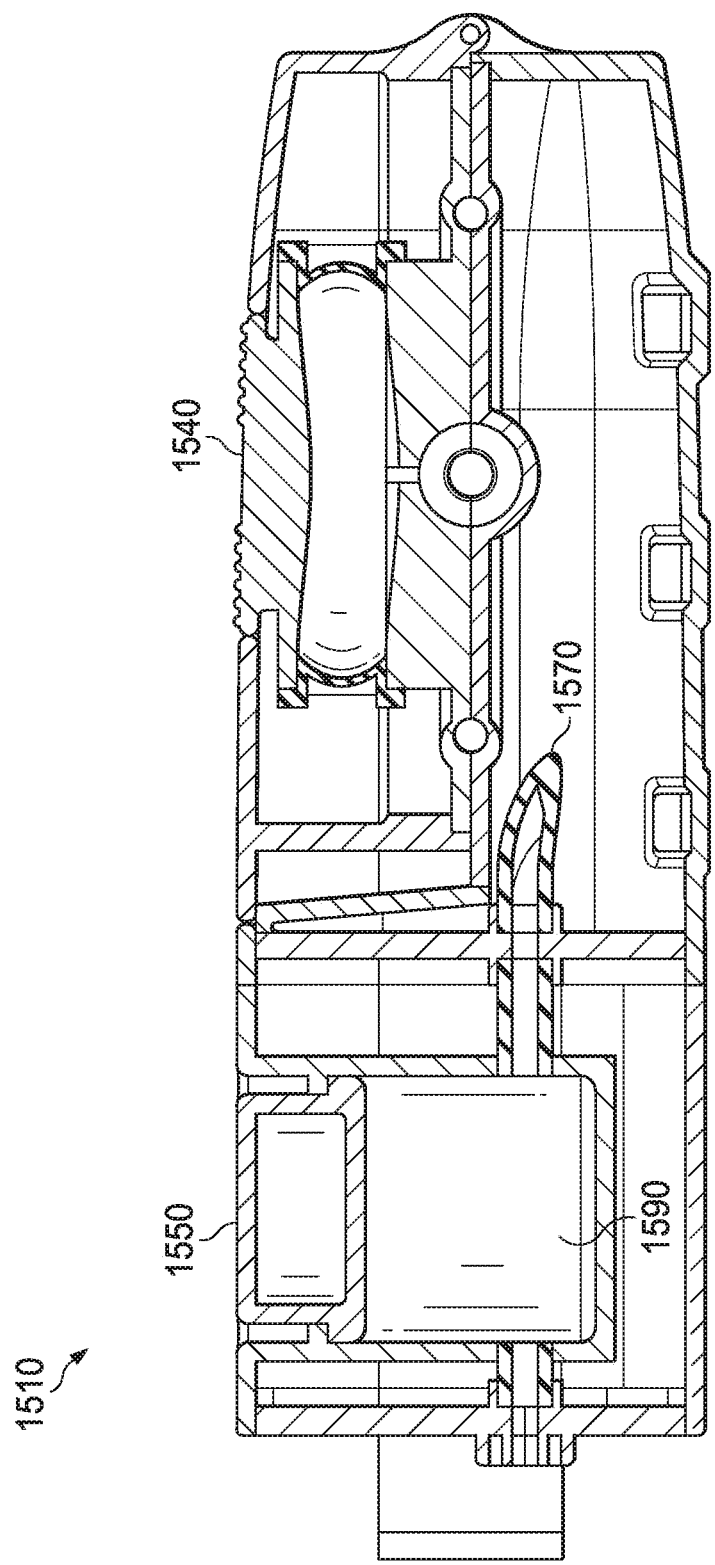
FIG. 15 illustrates a cross-section of one embodiment of the staging or "dual action" specimen delivery apparatus.

FIG. 15 illustrates a cross-section of one embodiment of the staging or dual action specimen delivery apparatus 1510. The first actuator 1540 (such as the previously described first bulb) propels a fluid through the fluid transport path. The propulsion may strip sample from clinical tool (e.g., swab) and otherwise mixes the fluid with the sample. The fluid and sample mixture are transported to the staging chamber 1590 via the fluid transport path which may include channels or fluid transport tubes such as rifled fluid transport tube 1570. When the specimen is ready to be delivered to the next stage of the medical diagnostic system, the user can depress the second actuator 1550. In the illustrated embodiment, the second actuator and staging chamber operate in a manner similar to a syringe to drive the prepared specimen from the staging chamber to the next stage of the medical diagnostic system.

In one embodiment, the next stage of the medical diagnostic system signals when it is ready to accept the specimen (i.e., when the user is cleared to depress the second actuator). In other embodiments, the next stage actively communicates with the specimen delivery apparatus through one or more ports on the backplane to either aid in the preparation of the specimen or to determine or signal when the specimen has been adequately prepared and is ready to be delivered to the next stage of the point-of-care medical diagnostic system.

For example, the staging chamber may be positioned adjacent a transducer for applying at least one of a thermal, mechanical, acoustical, or optical energy to the contents of the staging chamber. A thermal pad, for example, may be used to heat the contents of the staging chamber to a pre-determined temperature. Thermal, mechanical, or acoustical energy may be used for lysis.

The staging chamber may also be equipped with sensors to permit detection of threshold conditions that determine whether the specimen has been prepared appropriately. Sensor also enable controlled application of thermal, mechanical, acoustical, or optical energy to the contents of the staging chamber with the control provided by the next stage of the point-of-care medical diagnostic system. An optical sensor may be used to determine if certain chemical reactions are complete, for example. A thermal sensor may be used to monitor the temperature of the contents of the staging chamber. Power, sensor, and control signals may be communicated between the next stage and the specimen delivery apparatus through electrical ports on the backplane of the specimen delivery apparatus.

In the preceding detailed description, the invention is described with reference to specific exemplary embodiments thereof. A specimen delivery apparatus for in vitro medical diagnostic devices is described. The features of different embodiments disclosed may be combined in order to expand the versatility of the specimen delivery apparatus. Various modifications and changes may be made thereto without departing from the broader scope of the invention as set forth in the claims. The specification and drawings are, accordingly, to be regarded in an illustrative rather than a restrictive sense.

What is claimed is:

1. A specimen delivery apparatus for processing a biological specimen, the specimen delivery apparatus comprising:
   a housing having a first portion and a second portion, wherein the first portion is coupled to the second portion at a hinge, wherein the housing is operable to transition from an open state to a closed state when the second portion is rotated about the hinge toward the first portion, and wherein the housing further comprises
   an interfacing portion adjacent to the first portion and second portion, the interfacing portion including at least one fluid communication port;
   an intermediate portion positioned within the housing and having a cavity that forms a portion of a chamber for holding a sample, wherein the chamber is formed by closing the first portion with respect to the second portion, and wherein the intermediate portion and chamber are sealed within the housing in the closed state;
   a fluid transport path fluidly coupled to the cavity;
   a first bulb disposed within the housing and being coupled to the fluid transport path, wherein the first bulb is operable to propel a fluid within the specimen delivery apparatus along the fluid transport path when the housing is in a closed state and the first bulb is actuated; and
   a destructible seal coupled to the fluid transport path, the destructible seal being operable to prevent fluid communication through the at least one fluid communication port while the destructible seal is intact,
   wherein actuation of the first bulb communicates fluid through the at least one fluid communication port when the destructible seal is not intact.

2. The apparatus of claim 1, wherein the interfacing portion further comprises at least one attachment point for mechanically coupling the specimen delivery apparatus to a second apparatus, wherein the at least one fluid communication port of the specimen delivery apparatus is operable to align with a fluid communication port of the second apparatus to enable fluid communication between the apparatus and the another apparatus when coupled to each other via the at least one attachment point.

3. The apparatus of claim 1 further comprising a second bulb disposed to move fluid within the apparatus when the housing is in the closed state and the second bulb is actuated.

4. The apparatus of claim 1 further comprising an optical port operable to communicate optical energy to the cavity.

5. The apparatus of claim 4 wherein the optical port extends from the interfacing portion of the housing to the cavity.

6. The apparatus of claim 4 wherein the optical port extends from the cavity through one of the first portion and second portion of the housing.

7. The apparatus of claim 1 further comprising an electrical port operable to communicate electrical energy to the cavity.

8. The apparatus of claim 7 further comprising a heater operable to heat fluid within the cavity upon application of power to the electrical port.

9. The apparatus of claim 7 further comprising an acoustic transducer operable to communicate acoustic energy to a fluid within the cavity upon application of energy to the electrical port.

10. The apparatus of claim 7 wherein the electrical port is electrically coupled to the cavity and operable to communicate electrical energy to the cavity.

11. The apparatus of claim 7 further comprising a transducer coupled to the electrical port, wherein the transducer is operable to at least one of a thermal, mechanical, acoustical, and optical energy to the cavity upon the application of power to the electrical port.

12. The apparatus of claim 1, further comprising a fluid disposed proximate to the first bulb, the fluid being selected from the group consisting of a suspension solution, a reagent, and a solvent.

13. A specimen delivery apparatus for processing a biological specimen, the specimen delivery apparatus comprising:
- a housing including a first portion and a second portion, wherein the first portion is coupled to the second portion at a hinge, wherein the housing is operable to transition from an open state to a closed state when the second portion is rotated about the hinge toward the first portion, and wherein the housing further comprises an interfacing portion adjacent to the first portion and second portion, the interfacing portion including at least one fluid communication port;
- an intermediate portion positioned within the housing and having a cavity that forms a portion of a chamber for holding a sample, wherein the chamber is formed by closing the first portion with respect to the second portion, and wherein the intermediate portion and chamber are sealed within the housing when the housing is in the closed state;
- a fluid transport path fluidly coupled to the cavity;
- a cache comprising an enclosure for retaining and storing fluid and being coupled to the fluid transport path;
- a first bulb disposed along the fluid transport path and operable to propel a fluid within the apparatus along the fluid transport path when the housing is in a closed state and the first bulb is actuated, and wherein the cache is operable to receive and store a first portion of the fluid upon actuation of the first bulb; and
- a destructible seal coupled to the fluid transport path, the destructible seal being operable to prevent fluid communication through the at least one fluid communication port while the seal is intact,
- wherein the specimen delivery apparatus is operable to communicate a second portion of the fluid through the at least one fluid communication port when the destructible seal is not intact in response to actuation of the first bulb.

14. A specimen delivery apparatus comprising for processing a biological specimen, the specimen delivery apparatus comprising:
- a housing including a first portion and a second portion, wherein the first portion is coupled to the second portion at a hinge, wherein the housing is operable to transition from an open state to a closed state when the second portion is rotated about the hinge toward the first portion, and wherein the housing further comprises an interfacing portion adjacent to the first portion and second portion, the interfacing portion includes at least one fluid communication port;
- an intermediate portion positioned within the housing and having a cavity that forms a portion of a chamber for holding a sample, wherein the intermediate portion and chamber are sealed within the housing when the housing is in the closed state;
- a fluid transport path fluidly coupled to the cavity;
- a first bulb disposed along the fluid transport path and operable to a fluid within the apparatus along the fluid transport path when the housing is in a closed state in response to actuation of the first bulb;
- a retaining latch coupled to the first portion of the housing, wherein the retaining latch is operable to retain the first bulb in a compressed state following actuation of the first bulb; and
- a destructible seal coupled to the fluid transport path, the destructible seal being operable to prevent fluid communication through the at least one fluid communication port while the seal is intact, wherein the specimen delivery apparatus is operable to communicate fluid through the at least one fluid communication port when the destructible seal is not intact in response to actuation of the first bulb.

* * * * *